Nov. 15, 1949. M. B. FOSTER Plant Pat. 898
AECHMEA PLANT
Filed Sept. 17, 1948
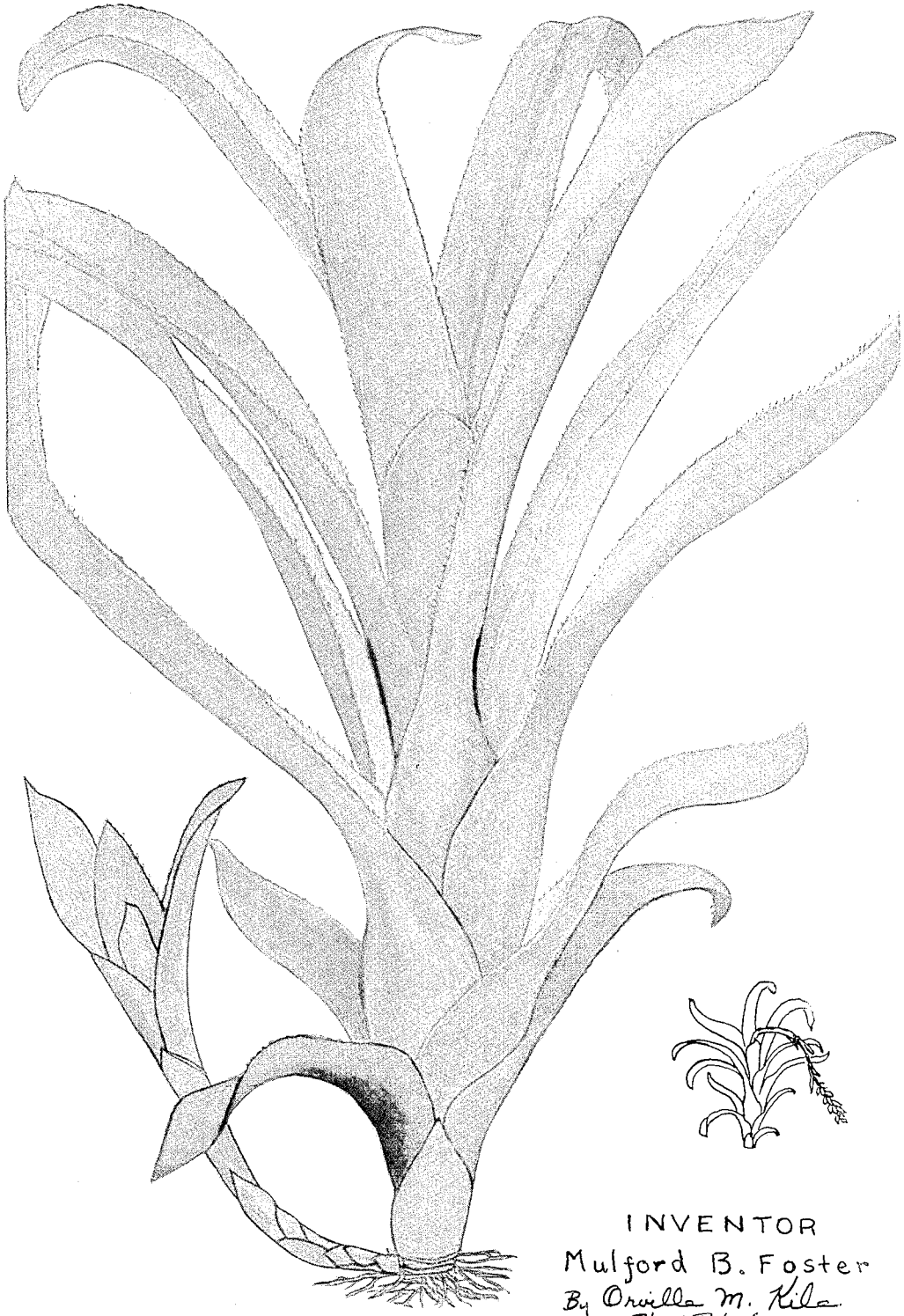
INVENTOR
Mulford B. Foster
By Orville M. Kile
Plant Pat. Agent Patented Nov. 15, 1949

Plant Pat. 898

UNITED STATES PATENT OFFICE

898

AECHMEA PLANT

Mulford B. Foster, Orlando, Fla.

Application September 17, 1948, Serial No. 49,777

1 Claim. (Cl. 47—59)

My present invention relates to a new and distinct variety of hybrid Aechmea plant. It was originated by me through the process of cross pollination of two new species of Aechmeas discovered by me in the jungles of Brazil. One of these parent plants is now known botanically as *Aechmea racinae* and the other as *Aechmea victoriana,* both named and published subsequent to my discovery of them.

I have reproduced asexually in my greenhouses in Orlando, Florida, considerable quantities of this new hybrid and its characteristics are definitely fixed.

My new variety is distinctly and outstandingly different from any Aechmea known or described, especially with respect to its leaf coloring and the formation of its inflorescence. It differs from both its parents in color and leaf shape as well as in its inflorescence. *Aechmea racinae* has light green leaves both on upper and under surface; the flowers consist of yellow and black petals with orange-red ovary and sepals. The inflorescence is pendent. *Aechmea victoriana,* the other parent, has bicolor leaves with fern green above and bronze red on the under side of leaf. The inflorescence is semi-pendent; the flower petals are dark purple with a white edge while the ovary and sepals are of a dark red color.

The accompanying illustration shows the form and coloring of the leaves of my new variety in natural tints although it gives only a faint idea of the glossy, almost varnished appearance that the leaves of this plant produce. When young the plant is often nearly all green but changes to its richness in color as it matures, often retaining one or more basal leaves of green.

Referring to the general structure of this new hybrid Aechmea, it is an herbaceous plant, and, although it is an epiphytic plant it quickly adapts itself to pot culture and makes an excellent house or dish garden plant. The natural formation of the leaves is such that a water-holding area is formed by the leaf sheath at the base of each leaf. This is common to most of the epiphytic members of the Bromeliaceae, the family to which this Aechmea hybrid belongs.

This new hybrid Aechmea more nearly resembles in form and color one of its parents, the *Aechmea victoriana.* However, it is much more vigorous in growth and larger in size, and the most outstandingly distinguishing character is the rich coloring of the leaves. These leaf colorings according to the Horticultural Colour Chart are shown as follows:

Small basal leaves: general representation of Fern Green No. 0862.

The few succeeding leaves: General representation of Currant Red No. 821, with shots of Fern Green near tips of leaves.

Balance of leaves: Currant Red 821 and Currant Red 821 with shots of Spanish Orange No. 010 and Burnt Orange No. 014.

These basic colors vary in tones and hues according to the light exposure in which the plants have been grown.

The long spike of small red and purple flowers needs no special description as this Aechmea hybrid plant will be grown more for its decorative foliage beauty than for its floral attributes.

The leaves as in all known Aechmea plants are edged with sharp spines, although they are not prominent on the leaf margins of this hybrid.

When this new hybrid is about two years old and after it has developed a flower spike, one or more new offshoots will be produced at the base of the plant as shown in the accompanying illustration. This is the only means of asexual propagation of this plant; being a hybrid it does not reproduce itself from its own seed.

Having thus disclosed my invention, I claim:

The new and distinct hybrid Aechmea plant as herein shown and described, characterized as to novelty by the distinctive glossy sheen and unusual red coloring of the leaves with this color equally brilliant on both sides of the leaves; its strong resistance to scale or other insect infestations; and its ability to thrive with a minimum of watering as it retains water in its leaf cups from only occasional waterings.

MULFORD B. FOSTER.

No references cited.